United States Patent [19]

Krasner et al.

[11] Patent Number: 4,796,623
[45] Date of Patent: Jan. 10, 1989

[54] CORNEAL VACUUM TREPHINE SYSTEM

[75] Inventors: Gary N. Krasner, Irvine; John W. Berkman, Costa Mesa, both of Calif.

[73] Assignee: The Cooper Companies, Inc., Menlo Park, Calif.

[21] Appl. No.: 75,842

[22] Filed: Jul. 20, 1987

[51] Int. Cl.[4] ............................................. A61F 17/32
[52] U.S. Cl. .................................... 128/305; 128/752; 604/22
[58] Field of Search ...................... 128/305, 305.1, 310, 128/751, 752, 753, 754, 755; 604/22

[56] References Cited

U.S. PATENT DOCUMENTS

| | | | |
|---|---|---|---|
| 2,838,050 | 6/1958 | Ara | 128/310 |
| 3,074,407 | 1/1963 | Moon et al. | 128/303 |
| 4,136,406 | 1/1979 | Norris | 128/303 |
| 4,205,682 | 6/1980 | Crock et al. | 128/305 |
| 4,336,805 | 6/1982 | Smirmaul | 128/310 |
| 4,423,728 | 1/1984 | Lieberman | 128/310 |
| 4,429,696 | 2/1984 | Hanna | 128/310 |
| 4,526,171 | 7/1985 | Schachar | 128/305 |
| 4,619,259 | 10/1986 | Graybill et al. | 128/305 |
| 4,665,914 | 5/1987 | Tanne | 128/745 |
| 4,688,570 | 8/1987 | Kramer et al. | 128/305 |

FOREIGN PATENT DOCUMENTS

| | | | |
|---|---|---|---|
| 3433581 | 3/1986 | Fed. Rep. of Germany | 128/305 |
| 3442339 | 5/1986 | Fed. Rep. of Germany | 128/305 |
| 3522998 | 1/1987 | Fed. Rep. of Germany | 128/305 |
| 1152587 | 4/1985 | U.S.S.R. | 128/305 |
| 1161106 | 6/1985 | U.S.S.R. | 128/305 |

OTHER PUBLICATIONS

R. J. Olson, "The Effect of Scleral Fixation Ring Placement and Trephine Tilting on Keroplasty Wound Size and Donor Shape", Jan. 1981, vol. 2, pp. 23–26.
P. C. Hessburg et al., "A Disposable Corneal Trephine", Opthalmic Surgery, Oct. 1980, vol. 11, No. 10, pp. 730–733.
R. J. Olson, "The Contact Lens Corneal Cutter: Accuracy and Reproducibility" Opthalmic Surgery, Mar. 1982, vol. 13, No. 3, pp. 210–211.
R. J. Olson, "Variation in Corneal Graft Size Related to Trephine Technique " Arch Opthalmol. vol. 97, Jul 1979, pp. 1323–1325.

*Primary Examiner*—Charles J. Myhre
*Assistant Examiner*—David A. Okonsky
*Attorney, Agent, or Firm*—Vorys, Sater, Seymour and Pease

[57] ABSTRACT

A corneal vacuum trephine system including a suction ring having an annular suction ring surface configured to define a suction annular space positionable against the eye. A vacuum device creates a vacuum in the suction annular space to secure the suction ring to the eye over the cornea. A trephine having a cutting edge is positionable so as to be movable relative to the suction ring for making with its cutting edge a circular cut in the cornea. A trephine guide is positionable on the suction ring for subsequently guiding the trephine therethrough and relative to the cornea. The guide permits the trephine to be separated from the suction ring after cutting the cornea when the suction ring is secured to the eye so that the cut in the cornea can be examined and the trephine positioned again in the suction ring precisely in the same place and orientation in the incomplete cornea cut to deepen the cut. The guide is also removable off of the suction ring when the ring is secured to the eye providing a large viewing area of the cornea through the bore of the suction ring. The guide and ring are configured to define a space therebetween through which the corneal cut made by the trephine and the cutting edge thereof can be seen with the ring in place on the eye and the trephine in the ring.

56 Claims, 4 Drawing Sheets

CORNEAL VACUUM TREPHINE SYSTEM

BACKGROUND OF THE INVENTION

The present invention relates to keratoplastic instruments for performing intraocular surgery and more particularly to such instruments and methods for performing penetrating keratoplasty utilizing corneal transplantation. It further concerns surgical apparatuses or trephines for precisely cutting out a small piece of the cornea.

Erasmus Darwin may have been the first to suggest in 1794 that a piece of a healthy cornea from a donor could be transplanted for a piece of unhealthy cornea in the recipient patient. This procedure can be used as when the unhealthy cornea has become opacifed or affected. In performing this transplant operation a corneal trephine is currently used to cut a circular disk or button from the corneal tissue.

Many designs for trephines are known and perhaps the simplest is a cylinder having an ultrasharp circular cutting edge at one end. This cylinder is positioned carefully over the cornea to be excised and with a downward pressure and a twisting or rotating of the cylinder the cutting edge will make a generally circular cut in the cornea. The cut can be made 360° all the way through the cornea into the interior chamber or an incomplete or partial cut can be made with the trephine and then the partial cut completed with curved corneal scissors.

In the early 1960s Jack Guyton, M.D., and John Balian, M.D., developed a trephine which would more effectively cut straight sides in the cornea. The underlying principle of their trephine was to provide suction to hold the eye up so that the trephine blade would penetrate the cornea without pushing down on the eye. By pushing down on the eye, non-parallel sides to the graft are invariably created. Their device comprised a floor-mounted motor driven corneal trephine in which a suction ring was provided to support the cornea and it was a rather cumbersome and complex device.

Many other simpler vacuum suction ring trephines have since been developed, and two of the trephines currently being sold which employ vacuums to secure the mechanism to the eye are the Hessberg-Baron and the Caldwell, both from Jed-Med, of St. Louis, Missouri. However, even these simpler and more developed vacuum type trephines suffer from many disadvantages. For example, the surgeon is able to see the cornea only through the narrow cylinder of the trephine in most of these designs either with this unaided eye or through a microscope. This makes it difficult to ensure the correct placement of the trephine on the cornea and also to orient the trephine at right angles to the plane of the iris. Further, it is difficult for the surgeon or his assistant to ascertain the depth of the cut which has been made with the known suction type trephines since only the inside area of the cut is visible through the narrow trephine cylinder. Since it is the tendency especially of the novice surgeon to not make a deep enough cut, and since this can often not be ascertained without removing the trephine from its position on the eye, the surgeon frequently must try to reposition the trephine in the exact same spot and with the exact same orientation as his initial cut to complete the cut. Of course, this is difficult if not impossible to do consistently. Other keratoplastic instrument designs are illustrated in U.S. Pat. No. 3,074,407, whose contents are hereby incorporated by reference in their entirety. Those designs though are rather complicated and do not appear to be easy to use in practice. They also do not provide for the repositioning of the trephine blade in the blade holder to complete an incomplete cut.

If the trephine is tilted relative to the plane of the iris then a generally oval wound or cut is produced. The greater the tilting, the greater (in an exponential relation) the difference in the lengths of the major and minor axes of this oval configuration result. The greater the amount of the tilt, the larger the resulting asphericity and resulting astigmatism.

OBJECTS AND SUMMARY OF THE INVENTION

Accordingly, a primary object of the present invention is to provide an improved trephine construction which remedies these disadvantages.

Another object of the present invention is to provide an improved vacuum suction type of trephine system.

A further object of the present invention is to provide an improved trephine system construction which allows for the better visualization of the trephine cutting blade and the corneal incision during the cutting procedure.

A still further object of the present invention is to provide an improved trephine system construction which allows for the more accurate positioning of the trephine with respect to the cornea to be excised.

Another object of the present invention is to provide an improved trephine system construction which allows for the accurate repositioning of the trephine in an incomplete cut to complete the cut.

A further object of the present invention is to provide an improved vacuum type trephine system which more accurately cuts a circular or nearly circular cut having only an inconsequential difference in the lengths of its major and minor axes.

A still further object of the present invention is to provide a vacuum suction trephine system of relatively simple construction and which is easy to use.

Directed to achieving the foregoing objects an improved corneal trephine system is provided by this invention. The system includes a vacuum suction ring defining a bore therethrough and positionable on the patient's eye over his cornea. A trephine guide means is removably supported on the suction ring and defines an elongated guide cylinder positionable with respect to the bore. A cylindrical trephine having a sharp circular corneal cutting edge at its distal end can be removably positioned in and guided by the guide cylinder. When the trephine is in the guide cylinder and rotated against the cornea, a corneal disk is thereby accurately cut. The corneal cut can be observed, with the suction ring secured by a vacuum force over the eye, either through the space defined between the guide cylinder and the suction ring or by removing the trephine guide means off of the suction ring and looking through the large space defined by the suction ring bore itself. The guide permits the cylindrical trephine to be separated from the ring after making a circular cut in the cornea, and with the suction ring secured over the eye, the cut examined, and if found to be too shallow, the trephine repositioned in the guide in precisely the same place and orientation in the incomplete corneal cut so that the cut can be deepened by again rotating the trephine.

Other objects and advantages of the present invention will become more apparent to those persons skilled in

DETAILED DESCRIPTION OF THE PREFERRED EMBODIMENTS

Figure 1:
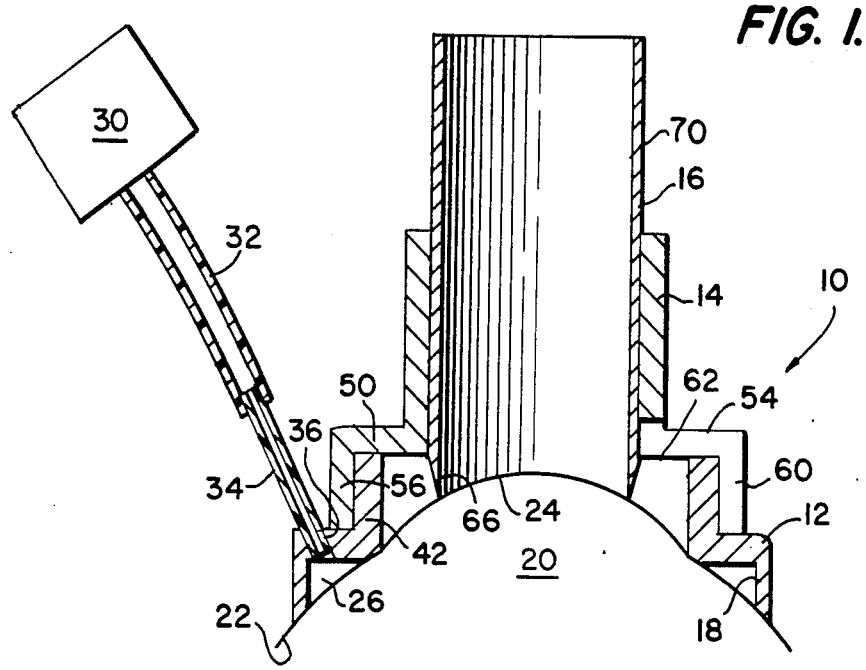
FIG. 1 is a longitudinal cross-sectional view of an assembled corneal vacuum trephine system of the present invention shown secured to the eye.

Referring to FIG. 1, a corneal vacuum trephine system of the present invention is illustrated generally at 10. Trephine system 10 comprises basically a sealing or suction ring 12, a trephine guard or guide 14 which is adapted to rest on the suction ring 12 and a trephine 16 which is adapted to fit into and rotate in the trephine guide 14.

Figure 2:
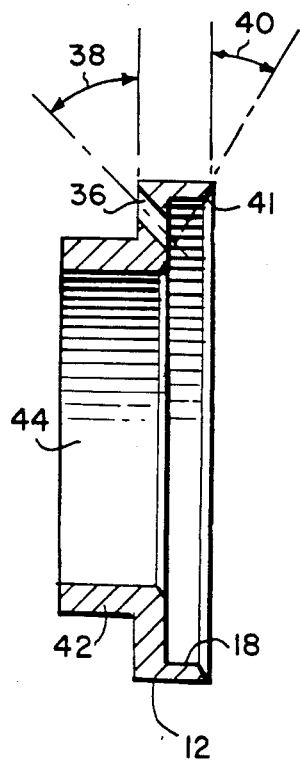
FIG. 2 is a side cross-sectional view of the suction ring of the system of FIG. 1 illustrated in isolation.
Figure 3:
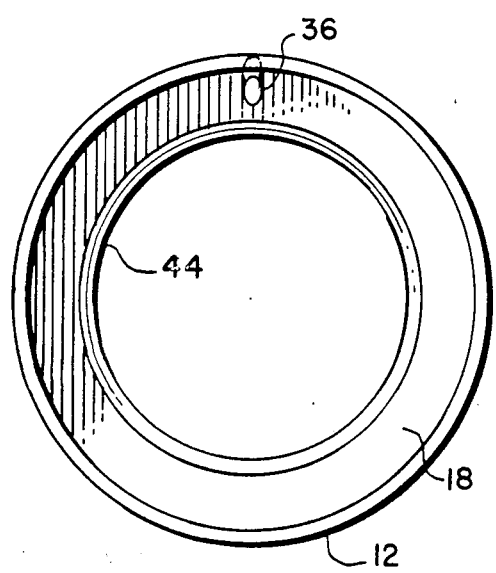
FIG. 3 is an end view of the suction ring of FIG. 2.

Suction ring 12, as best shown in FIG. 3, has an annular configuration and when viewed in cross section it is seen that the lower surface thereof has a stepped-in design to define an annular space or groove 18. When the suction ring 12 is positioned against the eye 20 over the cornea 24, the white sclera portion 22 of the eye defines the remaining boundary of the annular chamber 26. Then by applying a vacuum or suction force to this chamber 26 immediately before placement on the eye 20 or after placing it in position on the eye a vacuum is created therein and the resulting suction force holds the suction ring 12 securely in place on the eye. This suction is created by a suction device as shown generally and schematically in FIG. 1 at 30. The suction device 30 can be any suitable means for applying a slight vacuum and for example may be a rubber bulb, a conventional vacuum pump, or a spring-biased syringe. Vacuum device 30 can be connected via a flexible tube 32 which fits over another smaller tube 34 as shown in FIG. 1 which passes through a suction ring opening 36 of approximately 0.043 inches in diameter opening at an angle of about forty-five degrees as shown in FIG. 2 at 38 into the annular chamber 26. The angle, as designated in FIG. 2 at 40, of the bevel 41 of the suction ring 12 is thirty degrees. The suction ring 12 includes a narrower upwardly projecting cylinder 42 defining a bore 44 having a diameter of about half an inch. This half-inch diameter bore 44 with the trephine guide 14 and trephine 16 separated from the suction ring 12 provides a greater field of vision to the cornea 24 than by just viewing it through the trephine when positioning the suction ring 12 over the cornea 24 thereby allowing a quicker and more accurate positioning of the suction ring 12. Since the blade of the trephine 16 is relatively short and does not have a vacuum line attached to it, good visualization of the cut or incision made by it is possible. Suction ring 12 can be made of any suitable material including 303 stainless steel, and can be similar to the suction ring used by Barraquer Microkeratome from Steinway Instruments.

Figure 4:
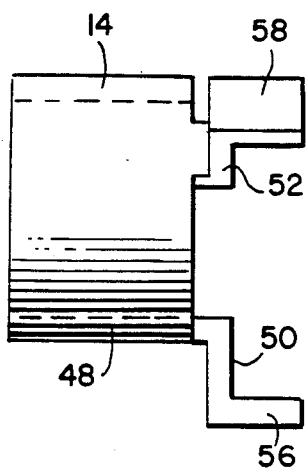
FIG. 4 is a side view of the trephine guide of the system of FIG. 1 illustrated in isolation.
Figure 5:
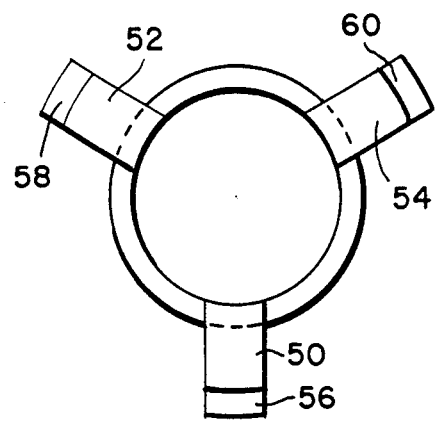
FIG. 5 is an end view of the trephine guide of FIG. 4.

The trephine guide 14 is best shown in FIGS. 4 and 5, and comprises a short cylinder 48 of having an inner diameter of 0.388 inches and having three equally-spaced legs 50, 52, 54 extending radially out therefrom. Each of the legs 50, 52, 54 has a downwardly depending foot, 56, 58, 60, respectively, each of which is configured and positioned to define an arc segment of the same circle, as best shown in FIG. 5, which has an inner diameter of 0.594 inches. The feet are adapted to fit snugly over the upwardly projecting cylinder 42 of the suction ring 12. Since the outer diameter of the cylinder 48 of the trephine guide 14 is 0.482 inches and the outer diameter of the bore 44 of the suction ring 12 is 0.740 inches, a space 62 is defined between them between each of the legs 50, 52, 54. It is through this space 62 that the circular cut including the outer edge thereof made by the cutting edge 66 of the trephine 16 can be seen with the suction ring 12 in place, and the outer edge of the cutting edge 66 of the trephine 16 can be seen as well. They can be visualized by the surgeon's assistant or technician during surgery to advise the surgeon as to the progress made in the cutting operation to ensure that a cut is formed which is neither too deep to injure the underlying ocular structure nor too shallow to excise the corneal tissue.

The cylinder 48 of the trephine guide 14 provides the guiding surface for the trephine 16 to hold it snugly so that it does not wobble but to not hold it so tightly that the trephine 16 cannot be inserted and rotated therein. Since the trephine guide 14 comprises a separate piece from the suction ring 12 and is securable thereto by the close fit of the leg and foot portions to the upwardly projecting cylinder 42, the trephine guide 14 can be removed or separated from the suction ring 12 so that the cornea and/or the cornea cut can be visualized through the wider field of the bore 44 of the suction ring 12. The trephine guide 14 can be formed from 303 stainless steel, and both the guide and suction ring should have a non-glare finish which resists autoclaving.

Figure 6:
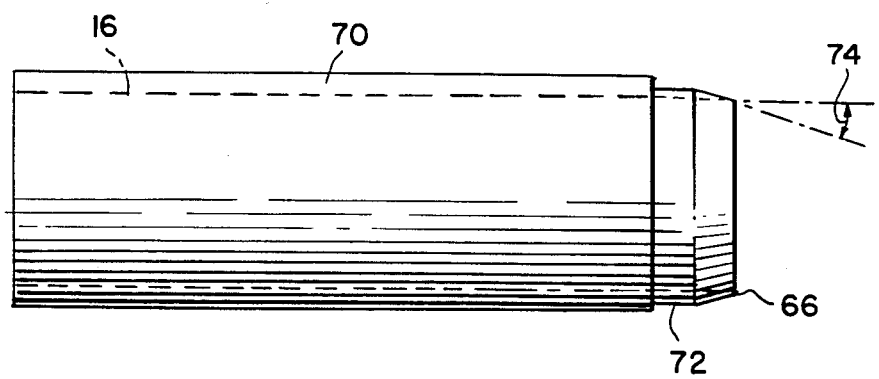
FIG. 6 is a side view of the trephine of the system of FIG. 1 illustrated in isolation.
Figure 7:
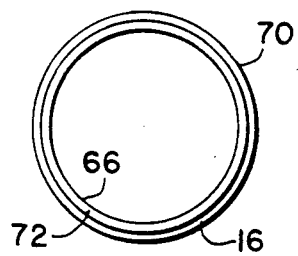
FIG. 7 is an end view of the trephine of FIG. 6.

Similarly, the trephine 16 fits through the cylinder 48 of the trephine guide and has an outer diameter only 0.001 of an inch less than the inner diameter of the cylinder 42 of the trephine guide 14. Thus, the trephine 16 can be easily inserted in the trephine guide 14 and removed therefrom, even when the suction ring 12 is secured to the eye. The trephine 16 very simply comprises a barrel portion 70 having a length of one to two inches, or 1.07 inches, and at its distal end a short slightly narrower barrel 72 and a cutting edge 66 angling in towards the center of the barrel 70 by an angle indicated in FIG. 6 at 74 of about seventeen degrees plus or minus two degrees. The cutting edge 66 must be ultra sharp since a dull blade can injure the ocular tissue. The trephine 16 can be constructed of 420 stainless steel.

An advantage of this system 10 over prior trephine systems is that the trephine 16 and the trephine guide 14 can be removed from the suction ring 12, the incision formed by the cutting edge 66 examined, and, if necessary, the trephine 16 and the trephine guide 14 returned to precisely the same place and orientation and the incision then made deeper. As can be appreciated, the system 10 must have its parts carefully manufactured and tolleranced so that the stack up between them make for a fit which is neither too loose nor too tight. The design of the present system 10 allows direct visualization of the cut through the bore of the trephine 16 and from the side through the space 62. Although the system 10 is designed for penetrating keratoplasty, i.e. full thickness corneal graft, which allows the surgeon to remove a disk of unhealthy cornea from the patient to be replaced by a donor tissue, it may also be used to make a partial thickness corneal incision like the type needed for epikeratophakia.

The procedure then for the present system 10 is to cover the patient with sterile drapes. A spring-assisted device is applied to help hold the eyelids of the eye 20 open. A wire rig is sutured to the white sclera 22 of the eye. The suction ring 12 is rested on the sclera 22 and using tweezers the globe of the eye 20 is positioned so that the suction ring 12 is positioned directly over the cornea. The surgeon's assistant then applies the vacuum to the annular chamber 26 via the vacuum device 30, such as by drawing a vacuum through a rubber bulb which communicates with the vacuum chamber 26 via the tubing 34. The position of the suction ring 12 with respect to the cornea 24 is then rechecked and adjusted by breaking and reapplying vacuum, if necessary. The trephine guide 14 is positioned on the suction ring 12 as shown in FIG. 1, and then the trephine 16 is slid into the cylinder 48 of the trephine guide 14. With gentle downward pressure, the trephine 16 is either twisted in a complete circular motion or rotated back and forth about the longitudinal axis of the trephine 16 so that a three hundred and sixty degree cut is made. This cut can be made all the way through the cornea 24 into the anterior chamber which would be indicated by a rush of fluid to the exterior of the eye, or alternatively, a shallower cut can be made until the first drop of acqueous fluid is observed by the surgeon or his assistant either through the bore of the trephine 16 or the space 62 and then the cut finished with surgical scissors. After the cut has been made with the trephine 16 the trephine guide 14 and trephine 16 can be removed to inspect the cut. As stated previously, if it is determined that the cut is too shallow, the trephine guide 14 and trephine 16 can then be placed back on the suction ring 12, and the cut deepened. Since the tolerances between the parts are very close and the suction ring 12 is securely fastened to the eye 20 then the repositioning of the trephine 16 will have the cutting edge 66 in precisely the same position and orientation as previously so that the cut can then be accurately and cleanly made deeper. The corneal disk cut by the present system 10 is then lifted off of the eye with forceps.

With most prior trephine systems the only visualization with the suction ring over the cornea is through the center of the trephine which provides only an eight millimeter field of vision. In contrast, with the trephine guide 14 and trephine 16 lifted off of the suction ring 12 of the present invention a twelve to fourteen millimeter opening through the bore of the suction ring 12 is defined which provides a wider field of vision allowing for the suction ring 12, and thereby the trephine 16 to be more accurately positioned on the eye.

From the foregoing detailed description it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

What is claimed is:

1. A corneal vacuum trephine system comprising:
   a suction ring adapted to be positioned on an eye over the cornea,
   said suction ring having an annular suction ring surface configured to define an annular suction space when said suction ring is positioned against the eye.
   said suction ring defining a suction ring bore,
   said annular suction space being positioned outside of and so as to generally not be in fluid communication with said suction ring bore,
   a trephine positionable in said suction ring bore and so as to be movable relative to said suction ring for cutting the cornea,
   said trephine comprising a generally cylindrical member and a sharp circular corneal cutting edge at the distal end of said cylindrical member for cutting a corneal disk by the rotation of said cylindrical member against the cornea,
   a trephine guide means positionable on said suction ring for guiding said trephine therein and for permitting said trephine to be separated from said suction ring when said suction ring is secured to the eye, and
   said trephine guide means defining an elongated guide cylinder for guiding said trephine therein.

2. The system of claim 1 wherein said guide cylinder is positioned within the cylinder defined by said suction ring bore.

3. The system of claim 1 wherein said trephine is positionable from a separated position relative to said suction ring to an inserted position in said suction ring while said suction ring is attached to the eye.

4. The system of claim 1 wherein said guide means is removable from said suction ring when said suction ring is attached to the eye.

5. The system of claim 1 wherein said trephine guide means defines a sleeve longitudinally down into which said cylindrical member and said cutting edge slide and in which said trephine is rotatable.

6. The system of claim 1 further comprising a vacuum means for providing a vacuum in said suction space when said suction ring is generally on the eye for securing said suction ring to the eye.

7. The system of claim 6 further comprising said vacuum means being external of said suction ring, and a tubing communicating said external vacuum means with said suction space.

8. The system of claim 1 wherein said suction ring defines a suction ring opening therethrough and into which said vacuum tubing is received, and said suction ring opening is positioned radially out from said trephine guide means and from said trephine when positioned in said trephine guide means.

9. The system of claim 1 wherein said cylinder extends only a small distance above the cornea for guiding generally the entire bottom portion of said cylindrical member.

10. The system of claim 9 wherein said trephine guide means includes a support member extending radially out from the base of said elongated cylinder.

11. The system of claim 10 wherein said support member rests directly on top of said suction ring.

12. A corneal vacuum trephine system comprising:
   a suction ring adapted to be positioned on an eye over the cornea,
   said suction ring having an annular suction ring surface configured to define an annular suction space when said suction ring is positioned against the eye.

said suction ring comprising a first ring portion defining an outside surface of said annular suction space and a second ring portion defining an inside surface of said annular suction space, said first and second ring portions being at right angles to one another, a trephine positionable so as to be movable relative to said suction ring for cutting the cornea, said trephine comprising a generally cylindrical member and a sharp circular corneal cutting edge at the distal end of said cylindrical member for cutting a corneal disk by the rotation of said cylindrical member against the cornea, and a trephine guide means positionable on said suction ring for guiding said trephine therein and for permitting said trephine to be separated from said suction ring when said suction ring is secured to the eye.

13. The system of claim 12 wherein said second ring portion defines a suction ring bore in which said trephine is positionable.

14. The system of claim 12 wherein said first ring portion defines a passageway therethrough through which a suction pressure can be applied to said suction space to securely hold said suction ring to the eye.

15. The system of claim 12 further comprising a vacuum means for providing a vacuum in said suction space when said suction ring is generally on the eye for securing said suction ring to the eye.

16. The system of claim 15 further comprising said vacuum means external of said suction ring, and a tubing communicating said external vacuum means with said suction space.

17. The system of claim 16 wherein said suction ring defines a suction ring opening therethrough and into which said vacuum tubing is received, and said suction ring opening is positioned radially out from said trephine guide means and from said trephine when positioned in said trephine guide means.

18. The system of claim 12 wherein said trephine is positionable from a separated position relative to said suction ring to an inserted position in said suction ring while said suction ring is attached to the eye.

19. The system of claim 12 wherein said guide means is removable from said suction ring when said suction ring is attached to the eye.

20. The system of claim 12 wherein said trephine guide means defines a sleeve longitudinally down into which said trephine slides and in which said trephine is rotatable.

21. The system of claim 12 wherein said trephine guide means comprises an elongated cylinder extending so as to be spaced only a small distance above the cornea for guiding therein the entire bottom portion of said cylinder.

22. The system of claim 21 wherein said elongated cylinder has a base, and said trephine guide means includes a support member extending radially out from said base of said elongated cylinder.

23. The system of claim 22 wherein said support member rests directly on top of said second ring portion.

24. A corneal vacuum trephine system comprising:
a suction ring adapted to be positioned on the eye over the cornea,
said suction ring having an annular suction ring surface configured to define a suction space positionable against the eye,
said suction ring defining a bore having a bore diameter.
a trephine positionable so as to be movable relative to said suction ring for cutting the cornea,
said trephine including a circular cutting edge at one end thereof,
a trephine guide means positionable on said suction ring for guiding said trephine therein and for permitting said trephine to be separated from said suction ring when said suction ring is secured to the eye,
said trephine guide means defining a trephine guide cylinder having an outer cylinder diameter,
said bore diameter being greater than said outer cylinder diameter, and
said trephine guide means including a support means for supporting said trephine guide cylinder so that said guide cylinder is positionable in the cylinder defined by said bore and such that a space is defined therebetween through which said circular cutting edge can be seen when said trephine is positioned in said trephine guide means.

25. The system of claim 24 wherein said support means positions said trephine guide cylinder concentrically within the cylinder defined by said bore.

26. The system of claim 24 wherein said support means comprises at least three spaced legs extending out from said trephine guide cylinder to contact said suction ring.

27. The system of claim 26 wherein said at least three spaced legs comprise three legs extending out from said trephine guide cylinder and spaced generally 120° relative to each other.

28. The system of claim 26 wherein said suction ring includes an upwardly projecting portion, and said legs rest on said upwardly projecting portion.

29. The system of claim 28 wherein said upwardly projecting portion is annular.

30. The system of claim 28 wherein said legs have downwardly depending foot portions at the outer ends thereof positionable directly outside of said upwardly projecting portion.

31. The system of claim 24 wherein said suction space has an annular configuration and said suction ring defines the inner and outer annular surfaces thereof.

32. The system of claim 24 further comprising a vacuum means for providing a vacuum in said suction space when said suction ring is generally on the eye for securing said suction ring to the eye.

33. The system of claim 32 including said vacuum means being external of said suction ring, a tubing communicating said external vacuum means with said suction space, said suction ring defining a suction ring opening therethrough and into which said vacuum tubing is received, and said suction ring opening being positioned radially out from said trephine guide means and from said trephine when positioned in said trephine guide means.

34. The system of claim 24 wherein said trephine is positionable from a separated position relative to said suction ring to an inserted position in said suction ring while said suction ring is attached to the eye.

35. The system of claim 24 wherein said guide means is removable from said suction ring when said suction ring is attached to the eye.

36. A corneal vacuum trephine system comprising:
a suction ring adapted to be positioned on the eye over the cornea, said suction ring having an annular suction ring surface configured to define a suction space positionable against the eye,
a trephine positionable so as to be movable relative to said suction ring for cutting the cornea,
a trephine guide means positionable on said suction ring for guiding said trephine therein and for permitting said trephine to be separated from said suction ring when said suction ring is secured to the eye,
said suction ring defining a bore having a bore diameter,
said trephine guide means defining a trephine guide cylinder having an outer cylinder diameter,
said trephine comprising a circular cutting edge at one end thereof,
said trephine guide means including a support means for supporting said trephine guide cylinder relative to said bore such that a space is defined therebetween through which said cutting edge of said trephine can be seen when said trephine is positioned in said trephine guide means, and
said support means comprising at least three spaced legs extending out from said trephine guide cylinder to contact said 37. The system of claim 36 wherein said at least three spaced legs comprise three legs extending out from said trephine guide cylinder and spaced generally 120° relative to each other.

38. The system of claim 36 wherein said suction ring includes an upwardly projecting portion, and said legs rest on said upwardly projecting portion.

39. The system of claim 38 wherein said upwardly projecting portion is annular.

40. The system of claim 38 wherein said legs have downwardly depending foot portions at the outer ends thereof positionable directly outside of said upwardly projecting portion.

41. The system of claim 36 wherein said bore diameter is greater than said outer cylinder diameter.

42. A corneal vacuum trephine system comprising:
a suction ring adapted to be positioned on an eye over the cornea,
said suction ring having an annular suction ring surface configured to define an annular suction space when said suction ring is positioned against the eye,
said suction ring defining a suction ring bore,
said annular suction space being positioned outside of and so as to generally not be in fluid communication with said suction ring bore,
a trephine positionable in said suction ring bore and so as to be movable relative to said suction ring for cutting the cornea,
said trephine comprising a generally cylindrical member and a sharp circular corneal cutting edge at the distal end of said cylindrical member for cutting a corneal disk by the rotation of said cylindrical member against the cornea,
a trephine guide means positionable on said suction ring for guiding said trephine therein and for permitting said trephine to be separated from said suction ring when said suction ring is secured to the eye, and
said trephine guide means defining a sleeve longitudinally down into which said cylindrical member and said cutting edge abuttingly slide and in which said trephine is rotatable.

43. A corneal vacuum trephine system comprising:
a suction ring adapted to be positioned on an eye over the cornea,
said suction ring having an annular suction ring surface configured to define an annular suction space when said suction ring is positioned against the eye,
said suction ring defining a suction ring bore,.
said annular suction space being positioned outside of and so as to generally not be in fluid communication with said suction ring bore,
a trephine positionable in said suction ring bore and so as to be movable relative to said suction ring for cutting the cornea,
said trephine comprising a generally cylindrical member and a sharp circular corneal cutting edge at the distal end of said cylindrical member for cutting a corneal disk by the rotation of said cylindrical member against the cornea,
a trephine guide means positionable on said suction ring for guiding said trephine therein and for permitting said trephine to be separated from said suction ring when said suction ring is secured to the eye, and
said trephine guide means comprising an elongated cylinder extending only a small distance above the cornea for guiding therein the entire bottom portion of said cylindrical member.

44. The system of claim 43 wherein said trephine guide means includes a support member extending radially out from the base of said elongated cylinder.

45. The system of claim 44 wherein said support member rests directly on top of said suction ring.

46. A corneal vacuum trephine system comprising:
a suction ring adapted to be positioned on an eye over the cornea,
said suction ring having an annular suction ring surface configured to define an annular surface of when said suction ring is positioned against the eye,
said suction ring comprising a first ring portion defining an outside surface of said annular suction space and a second ring portion defining an inside surface of said annular suction space,
a trephine positionable so as to be movable relative to said suction ring for cutting the cornea,
said trephine comprising a generally cylindrical member and a sharp circular corneal cutting edge at the distal end of said cylindrical member for cutting a corneal disk by the rotation of said cylindrical member against the cornea,
a trephine guide means positionable on said suction ring for guiding said trephine therein and for permitting said trephine to be separated from said suction ring when said suction ring is secured to the eye, and
said trephine guide means defining a sleeve longitudinally down into which said trephine abbutingly slides and in which said trephine is rotatable.

47. The system of claim 46 wherein said second ring portion defines a suction ring bore in which said trephine is positionable.

48. The system of claim 46 wherein said first ring portion defines a passageway therethrough through which a suction pressure can be applied to said suction space to securely hold said suction ring to the eye.

49. The system of claim 46 further comprising a vacuum means for providing a vacuum in said suction space when said suction ring is generally on the eye for securing said suction ring to the eye.

50. The system of claim 49 further comprising said vacuum means being external of said suction ring, and a tubing communicating said external vacuum means with said suction space.

51. The system of claim 50 wherein said suction ring defines a suction ring opening therethrough and into which said vacuum tubing is received, and said suction ring opening is positioned radially out from said trephine guide means and from said trephine when positioned in said trephine guide means.

52. The system of claim 46 wherein said trephine is positionable from a separated position relative to said suction ring to an inserted position in said suction ring while said suction ring is attached to the eye.

53. The system of claim 12 wherein said guide means is removable from said suction ring when said suction ring is attached to the eye.

54. A corneal vacuum trephine system comprising:
a suction ring adapted to be positioned on an eye over the cornea,
said suction ring having an annular suction ring surface configured to define an annular suction space when said suction ring is positioned against the eye,
said suction ring comprising a first ring portion defining an outside surface of said annular suction space and a second ring portion defining an inside surface of said annular suction space,
a trephine positionable so as to be movable relative to said suction ring for cutting the cornea,
said trephine comprising a generally cylindrical member and a sharp circular corneal cutting edge at the distal end of said cylindrical member for cutting a corneal disk by the rotation of said cylindrical member against the cornea,
a trephine guide means positionable on said suction ring for guiding said trephine therein and for permitting said trephine to be separated from said suction ring when said suction ring is secured to the eye, and
said trephine guide means comprising an elongated cylinder extending so as to be spaced only a small distance above the cornea for guiding therein the entire bottom portion of said cylindrical member.

55. The system of claim 54 wherein said cylinder has a base, and said trephine guide means includes a support member extending radially out from said base of said cylinder.

56. The system of claim 55 wherein said support member rests directly on top of said second ring portion.

* * * * *